(12) United States Patent
Yasumura et al.

(10) Patent No.: US 10,376,830 B2
(45) Date of Patent: Aug. 13, 2019

(54) GAS ANALYSIS SYSTEM, LIQUID SEPARATOR, AND GAS ANALYZER

(71) Applicant: NIHON KOHDEN CORPORATION, Shinjuku-ku, Tokyo (JP)

(72) Inventors: Satoshi Yasumura, Tokyo (JP); Katsumi Nakaichi, Tokyo (JP); Shinya Suzuki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 172 days.

(21) Appl. No.: 15/614,709

(22) Filed: Jun. 6, 2017

(65) Prior Publication Data

US 2017/0361269 A1    Dec. 21, 2017

(30) Foreign Application Priority Data

Jun. 16, 2016 (JP) ................. 2016-120195

(51) Int. Cl.
*A61B 5/097* (2006.01)
*B01D 17/06* (2006.01)
(Continued)

(52) U.S. Cl.
CPC .............. *B01D 53/30* (2013.01); *A61B 5/082* (2013.01); *A61B 5/097* (2013.01);
(Continued)

(58) Field of Classification Search
CPC ........... A61B 5/097; A61B 5/082; A61B 5/05; A61B 2503/045; A61B 2562/0223;
(Continued)

(56) References Cited

U.S. PATENT DOCUMENTS 3,698,159 A * 10/1972 Ruse ...................... B01D 45/08
422/90
4,997,463 A * 3/1991 Ricciardelli ........... A61B 5/097
128/205.12
(Continued)

FOREIGN PATENT DOCUMENTS

| JP | 357054859 | * | 4/1982 |
| WO | 2013-070545 A1 | | 5/2013 |
| WO | 2014-068000 A1 | | 5/2014 |

OTHER PUBLICATIONS

Extended European Search Report issued in Patent Application No. EP 17 17 4715 dated Nov. 7, 2017.
(Continued)

*Primary Examiner* — Jacques M Saint Surin
(74) *Attorney, Agent, or Firm* — Pearne & Gordon LLP

(57) ABSTRACT

A gas analysis system includes a gas analyzer which analyzes a gas acquired from a living body and a liquid separator which is detachably attached to the gas analyzer, and which separates a liquid component from the gas. In the gas analysis system, the liquid separator includes a magnet, and the gas analyzer includes a magnetic sensor which detects magnetism generated by the magnet, and a determining section which, based on the magnetism detected by the magnetic sensor, determines that the liquid separator is attached to the gas analyzer.

11 Claims, 2 Drawing Sheets

(51) Int. Cl.
*A61B 5/08* (2006.01)
*A61M 16/08* (2006.01)
*B01D 53/30* (2006.01)
*A61B 5/05* (2006.01)
*A61M 16/00* (2006.01)

(52) U.S. Cl.
CPC ......... *A61M 16/0808* (2013.01); *B01D 17/06* (2013.01); *A61B 5/05* (2013.01); *A61B 2503/045* (2013.01); *A61B 2562/0223* (2013.01); *A61B 2562/0247* (2013.01); *A61M 2016/0027* (2013.01); *A61M 2205/7536* (2013.01); *A61M 2230/437* (2013.01)

(58) Field of Classification Search
CPC ............ A61B 2562/0247; B01D 17/06; B01D 53/30; A61M 16/0808; A61M 2230/437; A61M 2016/0027; A61M 2205/7536
USPC .......................................................... 73/23.2
See application file for complete search history.

(56) References Cited

U.S. PATENT DOCUMENTS

| | | | |
|---|---|---|---|
| 6,896,713 | B1 | 5/2005 | Eckerbom et al. |
| 8,720,442 | B2* | 5/2014 | Perine ............... A61M 16/0816 128/204.18 |
| 9,649,458 | B2* | 5/2017 | Andrieux ........... A61M 16/0051 |
| 9,861,298 | B2* | 1/2018 | Eckerbom .............. A61B 5/097 |
| 2002/0062702 | A1* | 5/2002 | Bradley ............... G01N 1/2214 73/864.34 |
| 2003/0191405 | A1 | 10/2003 | Rich et al. |
| 2012/0151990 | A1* | 6/2012 | Viitala .................. A61B 5/097 73/23.3 |

OTHER PUBLICATIONS

Communication pursuant to Article 94(3) EPC issued in Patent Application No. EP 17 174 715.7 dated Feb. 1, 2019.

* cited by examiner

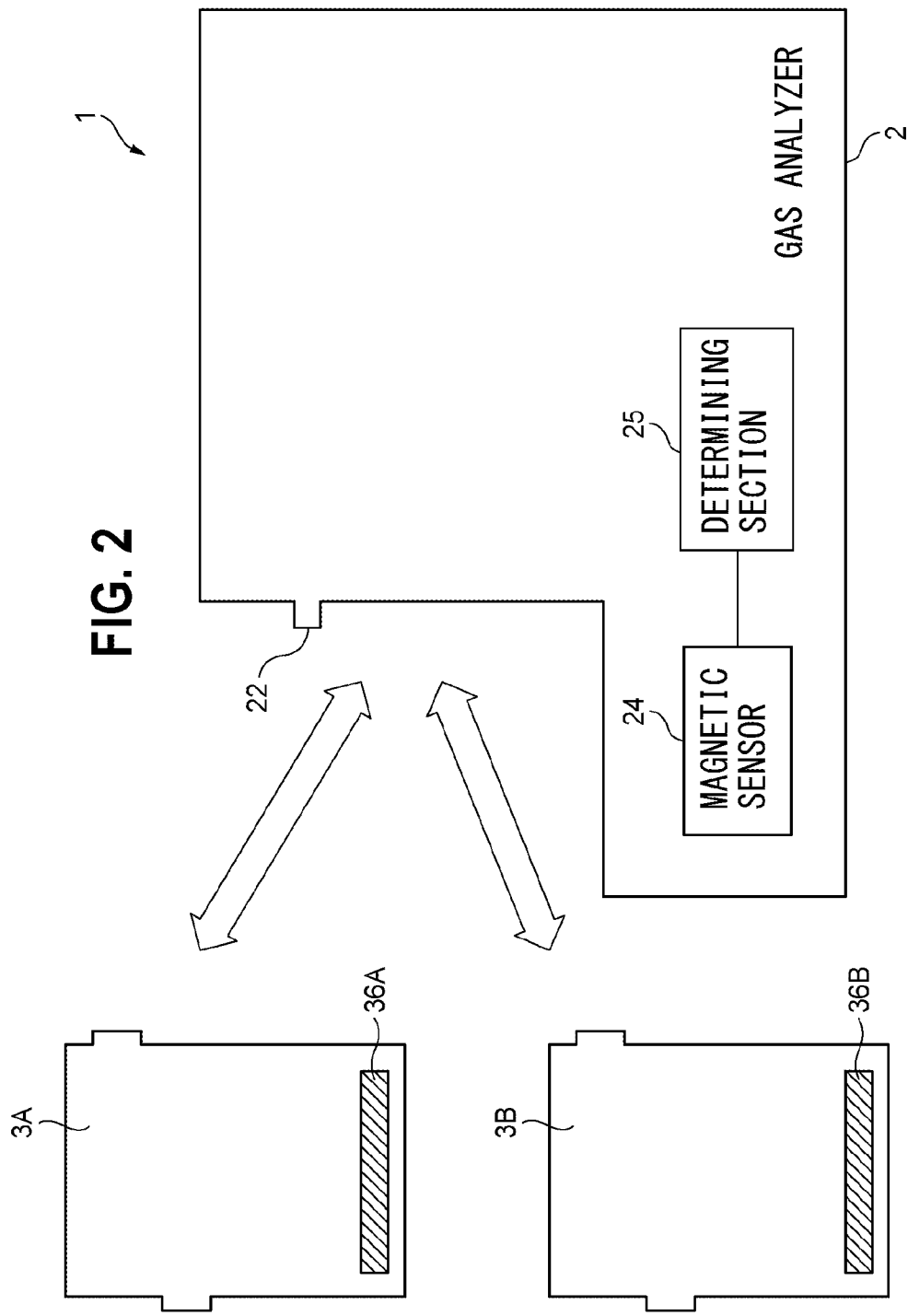

GAS ANALYSIS SYSTEM, LIQUID SEPARATOR, AND GAS ANALYZER

CROSS REFERENCE TO RELATED APPLICATION

This application is based on Japanese Patent Applications No. 2016-120195 filed on Jun. 16, 2016, the contents of which are incorporated herein by reference.

BACKGROUND

1. Technical Field

The present invention relates to a gas analyzer which analyzes a gas acquired from a living body. The invention further relates to a liquid separator which is to be detachably attached to such a gas analyzer, and which separates the liquid component from the gas. The invention still further relates to a gas analysis system which includes the gas analyzer and the liquid separator.

2. Background Art

As an example of a gas analyzer of this type, an apparatus is known which acquires a respiratory gas from a patient under surgery, and which measures the concentration of anesthesia gas contained in the respiratory gas.

In order to prevent water vapor contained in the respiratory gas from being condensed and entering the interior of the gas analyzer, a liquid separator which is also called a water trap is attached to the gas analyzer. The liquid separator includes a hydrophobic filter. The water content contained in the respiratory gas of the patient is captured by the filter, and blocked from entering the gas analyzer. Such a liquid separator is disclosed, for example, in U.S. Pat. No. 6,896,713.

The liquid separator and gas analysis instrument which are disclosed in U.S. Pat. No. 6,896,713 include electric contacts, respectively. When the electric contacts are contacted with each other, it is detected that the liquid separator is attached to the gas analysis instrument. In the configuration depending on an electrical contact, an error in detection of the attachment state may be possibly caused by a contact failure.

It is an object of the invention to improve the accuracy of detection of an attachment state of a liquid separator with respect to a gas analyzer.

SUMMARY OF THE INVENTION (1) According to an aspect of the invention, a gas analysis system includes a gas analyzer which analyzes a gas acquired from a living body and a liquid separator which is detachably attached to the gas analyzer, and which separates a liquid component from the gas. In the gas analysis system, the liquid separator includes a magnet, and the gas analyzer includes a magnetic sensor which detects magnetism generated by the magnet, and a determining section which, based on the magnetism detected by the magnetic sensor, determines that the liquid separator is attached to the gas analyzer.

According to the configuration (1), the attachment state of the liquid separator with respect to the gas analyzer can be detected in a non-contact manner. Unlike the technique which depends on an electrical contact, therefore, there is no possibility that an error in detection of the attachment state is caused by a contact failure. Consequently, the accuracy of detection of the attachment state of the liquid separator with respect to the gas analyzer can be improved.

(2) According to another aspect of the invention, a liquid separator is to be detachably attached to a gas analyzer that analyzes a gas acquired from a living body, and separates a liquid component from the gas. Further, the liquid separator includes a magnet which generates magnetism that is to be detected by a magnetic sensor provided in the gas analyzer.

(3) According to another aspect of the invention, a gas analyzer to which a liquid separator separating a liquid component from a gas acquired from a living body is detachably attached includes a magnetic sensor and a determining section. The magnetic sensor detects magnetism generated by a magnet provided in the liquid separator, and the determining section determines that the liquid separator is attached to the gas analyzer based on the magnetism detected by the magnetic sensor.

BRIEF DESCRIPTION OF DRAWINGS

FIG. 2 is a diagram illustrating the operation of the gas analysis system.

DETAILED DESCRIPTION OF EMBODIMENTS

Figure 1:
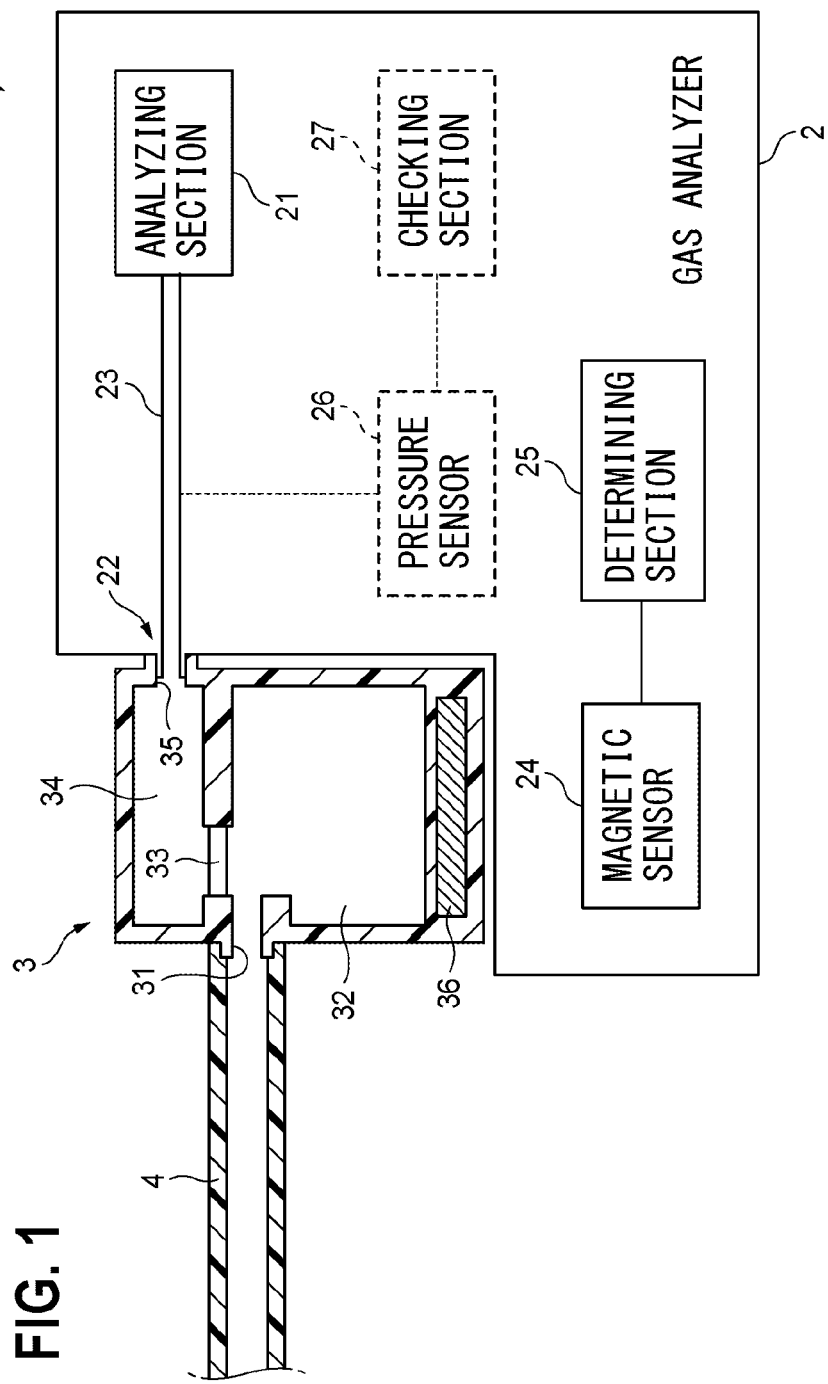
FIG. 1 is a diagram showing the functional configuration of a gas analysis system of an embodiment.

Hereinafter, an embodiment will be described in detail with reference to the accompanying drawings. FIG. 1 shows the functional configuration of a gas analysis system of the embodiment. The gas analysis system 1 includes a gas analyzer 2 and a liquid separator 3.

The gas analyzer 2 includes an analyzing section 21 and an interface 22. The liquid separator 3 is configured so as to be attachable to and detachable from the interface 22 of the gas analyzer 2. The liquid separator 3 is configured so as to separate a liquid component from a gas acquired from a living body.

The liquid separator 3 includes an introduction port 31. A sampling tube 4 for guiding a respiratory gas (an example of the gas) of a patient (an example of the living body) is detachably connected to the introduction port 31.

The liquid separator 3 includes a reservoir 32, a hydrophobic filter 33, and a gas passage 34. The introduction port 31 is opened in the reservoir 32. The hydrophobic filter 33 separates the reservoir 32 and the gas passage 34 from each other.

The liquid separator 3 includes a discharge port 35. The discharge port 35 communicates with the gas passage 34. The discharge port 35 is configured so as to be connectable to the interface 22 of the gas analyzer 2.

The gas analyzer 2 includes a gas flow path 23. The analyzing section 21 and the interface 22 communicate with each other via the gas flow path 23. When the discharge port 35 of the liquid separator 3 is connected to the interface 22, a flow path extending from the sampling tube 4 which is connected to the patient, to the analyzing section 21 through the liquid separator 3 is formed.

The gas analyzer 2 includes a pump and suction interface which are not shown. The pump and the suction interface communicate with each other. On the other hand, the liquid separator 3 includes a suction port which is not shown. The suction port and the gas passage 34 communicate with each other. When the liquid separator 3 is attached to the gas analyzer 2, the suction port is connected to the suction interface. As a result, a gas flow path extending from the gas passage 34 to the pump is formed.

When the pump operates, a gas flow extending from the introduction port 31 to the discharge port 35 through the reservoir 32 and the gas passage 34 is produced. The water content (an example of the liquid component) contained in the respiratory gas of the patient which is introduced into the liquid separator 3 through the introduction port 31 is blocked from passage by the hydrophobic filter 33, and accumulated in the reservoir 32.

The respiratory gas of the patient from which the water content is removed is sucked into the gas analyzer 2 from the discharge port 35 connected to the interface 22. The respiratory gas passes through the gas flow path 23 to reach the analyzing section 21. The analyzing section 21 is configured so as to analyze concentrations of carbon dioxide, oxygen, nitrous oxide, a volatile anesthetic agent, and the like which are contained in the respiratory gas.

The liquid separator 3 includes a magnet 36. The gas analyzer 2 includes a magnetic sensor 24 and a determining section 25. The magnetic sensor 24 is configured so as to detect magnetism generated by the magnet 36. The determining section 25 is configured so as to determine that the liquid separator 3 is attached to the gas analyzer 2, based on the magnetism detected by the magnetic sensor 24.

When the liquid separator 3 is attached to the gas analyzer 2, the magnet 36 approaches the magnetic sensor 24. This causes the magnitude of the magnetism detected by the magnetic sensor 24, to be increased. For example, the determining section 25 can be configured so as to, in the case where the magnitude of the magnetism detected by the magnetic sensor 24 exceeds a threshold, determine that the liquid separator 3 is attached to the gas analyzer 2.

The analyzing section 21 can be configured so as to perform a predetermined analysis, only in the case where the determining section 25 determines that the liquid separator 3 is attached to the gas analyzer.

According to the configuration, the attachment state of the liquid separator 3 with respect to the gas analyzer 2 can be detected in a non-contact manner. Unlike the technique which depends on an electrical contact, there is no possibility that an error in detection of the attachment state is caused by a contact failure. Consequently, the accuracy of detection of the attachment state of the liquid separator 3 with respect to the gas analyzer 2 can be improved.

The gas analysis system 1 of the embodiment can be configured so that, as shown in FIG. 2, plural types of liquid separators can be attached to the gas analyzer 2. For example, a liquid separator 3A for an adult, and a liquid separator 3B for a neonate can be attached to the gas analyzer 2.

The liquid separator 3A includes a magnet 36A. The magnet 36A is disposed in the liquid separator 3A so that, for example, the N pole of the magnet 36A is directed toward the magnetic sensor 24 when the liquid separator 3A is attached to the gas analyzer 2. The liquid separator 3B includes a magnet 36B. The magnet 36B is disposed in the liquid separator 3B so that, for example, the S pole of the magnet 36B is directed toward the magnetic sensor when the liquid separator 3B is attached to the gas analyzer 2.

In this case, the magnetic sensor 24 of the gas analyzer 2 is configured so as to detect the polarity which is exhibited by a magnet. The determining section 25 of the gas analyzer 2 is configured so as to determine the type of the attached liquid separator based on the magnet polarity detected by the magnetic sensor 24. In the example, when the magnetic sensor 24 detects the N pole, the determining section 25 determines that the liquid separator 3A for an adult is attached. When the magnetic sensor 24 detects the S pole, the determining section 25 determines that the liquid separator 3B for a neonate is attached. In other words, the polarity of each of the magnets 36A and 36B indicates the type of the liquid separator to which the magnet itself is attached.

In a system in which the attachment state of a liquid separator is detected by means of an electrical contact, in the case where also the type of the liquid separator is to be detected, at least one electric contact for detecting the type is necessary in addition to an electric contact for detecting the attachment state. In the configuration of the embodiment, by contrast, both the attachment state of the liquid separator 3 with respect to the gas analyzer 2, and the type of the liquid separator can be detected simply by disposing one magnet and one magnetic sensor. The number of components related to the detection is reduced, and therefore the possibility of occurrence of a failure or the like in the detection function can be lowered.

In the case where it is necessary to detect only the polarity of the magnet, an inexpensive Hall element can be used as the magnetic sensor 24. Therefore, the cost can be reduced in both the gas analyzer 2 and the liquid separator 3, with the result that the cost of constructing the gas analysis system 1 can be suppressed.

As shown in FIG. 1, the gas analyzer 2 can include a pressure sensor 26 and a checking section 27. The pressure sensor 26 is configured so as to detect the pressure of the gas flow path 23. The checking section 27 is configured so as to check whether the liquid separator 3 is correctly attached or not, based on a change of the pressure detected by the pressure sensor 26.

In the case where the discharge port 35 of the liquid separator 3 is not correctly connected to the interface 22 of the gas analyzer 2, even when the pump operates, for example, the pressure of the gas flow path 23 does not show a predetermined change. The checking section 27 is configured so as to, in the case where such a situation occurs, detect an abnormality in the attachment of the liquid separator 3.

According to the configuration, while a non-contact detection system is employed, it is possible to detect more surely that the liquid separator 3 is correctly attached to the gas analyzer 2. That is, the accuracy of detection of the attachment state of the liquid separator 3 with respect to the gas analyzer 2 can be further improved.

For example, the analyzing section 21 may be configured so as to, only when the determining section 25 determines that the liquid separator 3 is attached, and the checking section 27 confirms the correct attachment of the liquid separator 3, perform a predetermined analysis. In the case where an abnormality in the attachment of the liquid separator 3 is detected, at least one of visual notification, auditory notification, and notification by communication to an external apparatus (such as a patient monitor) may be performed.

The above-described embodiment is a mere example for facilitating understanding of the invention. The configuration of the embodiment may be adequately changed or improved without departing the spirit of the invention. It is obvious that equivalents are included within the technical scope of the invention.

In the embodiment, the type of the liquid separator 3, i.e. the type for an adult, or that for a neonate is indicated depending on the polarity of the magnet 36 provided in the liquid separator 3. However, the type of the liquid separator 3 which is indicated by the polarity of the magnet 36 is adequately determined in accordance with the specification of the liquid separator 3 that is used in the gas analysis system 1.

In the embodiment, the type of the liquid separator 3 which is indicated by the magnet 36 provided in the liquid separator 3 is classified into two categories respectively corresponding to the possible polarities of the magnet 36. If the magnetic sensor 24 can be configured so as to distinguish magnitudes of the magnetic force in addition to or in place of the polarities, however, the type of the liquid separator 3 may be classified into three or more categories. Also in this case, both the attachment state of the liquid separator 3 with respect to the gas analyzer 2, and the type of the liquid separator can be detected simply by disposing one magnet and one magnetic sensor.

In the embodiment, the water content contained in the respiratory gas of the patient is separated by the liquid separator 3. As far as the liquid component to be separated can be separated by the hydrophobic filter 33 of the liquid separator 3, the gas to be acquired is not limited to the respiratory gas, and the liquid component to be separated is not limited to the water content.

Although the embodiment is applied to the analysis in which a gas acquired from the human body is analyzed by the analyzing section 21, the invention may be applied also to an analysis in which a gas acquired from the body of an animal other than a human is analyzed by the analyzing section 21.

What is claimed is:

1. A gas analysis system comprising:
    a gas analyzer which analyzes a gas acquired from a living body; and
    a liquid separator which is detachably attached to the gas analyzer, and which separates a liquid component from the gas, wherein:
    the liquid separator includes a magnet configured to indicate a type of the liquid separator, and
    the gas analyzer includes:
        a magnetic sensor which detects magnetism generated by the magnet and a polarity of the magnet; and
        a determining section which determines an attachment state of the liquid separator and the type of the liquid separator based on an amplitude of the magnetism and the polarity of the magnet detected by the magnetic sensor.

2. The gas analysis system according to claim 1, wherein the magnetic sensor includes a Hall element which detects the polarity of the magnet.

3. The gas analysis system according to claim 1, wherein the type includes a type for an adult and a type for a neonate.

4. The gas analysis system according to claim 1, wherein the gas analyzer further includes:
    a pressure sensor that detects a pressure of a flow path through which the gas flows; and a checking section that checks whether the liquid separator is correctly attached or not, based on a change of the pressure detected by the pressure sensor.

5. A liquid separator configured to be detachably attached to a gas analyzer that analyzes a gas acquired from a living body, and which separates a liquid component from the gas, wherein:
    the liquid separator includes a magnet which generates a magnetism, the magnetism indicating a type of the liquid separator, and a polarity of the magnet being detected by a magnetic sensor provided in the gas analyzer, and
    an attachment state of the liquid separator and the type of the liquid separator are determined based on an amplitude of the magnetism and the polarity of the magnet.

6. The liquid separator according to claim 5, wherein the polarity of the magnet is set to indicate the type.

7. The liquid separator according to claim 5, wherein the type includes a type for an adult and a type for a neonate.

8. A gas analyzer to which a liquid separator is configured to be detachably attached, the liquid separator separating a liquid component from a gas acquired from a living body, wherein the gas analyzer includes:
    a magnetic sensor which detects magnetism generated by a magnet provided in the liquid separator and which detects a polarity of the magnet; and
    a determining section which determines an attachment state of the liquid separator and a type of the liquid separator based on an amplitude of the magnetism and the polarity of the magnet detected by the magnetic sensor.

9. The gas analyzer according to claim 8, wherein the magnetic sensor is a Hall element which detects the polarity that is exhibited by the magnet.

10. The gas analyzer according to claim 8, wherein the type includes a type for an adult and a type for a neonate.

11. The gas analyzer according to claim 8, wherein the gas analyzer further includes:
    a pressure sensor that detects a pressure of a gas flow path through which the gas flows; and
    a checking section that checks whether the liquid separator is correctly attached or not, based on a change of the pressure detected by the pressure sensor.

* * * * *